(12) United States Patent
Vollkron et al.

(10) Patent No.: US 8,521,265 B2
(45) Date of Patent: Aug. 27, 2013

(54) HEART MONITOR

(75) Inventors: Michael Vollkron, Pressbaum (AT); Gerald Czygan, Buckenhof (DE); Thomas Kraemer, Nuremberg (DE); Michael Lippert, Ansbach (DE); Olaf Skerl, Bad Doberan (DE)

(73) Assignee: Biotronik CRM Patent AG, Baar (CH)

(*) Notice: Subject to any disclaimer, the term of this patent is extended or adjusted under 35 U.S.C. 154(b) by 820 days.

(21) Appl. No.: 12/749,723

(22) Filed: Mar. 30, 2010

(65) Prior Publication Data

US 2010/0268294 A1    Oct. 21, 2010

(30) Foreign Application Priority Data

Apr. 15, 2009  (DE) .......................... 10 2009 002 397

(51) Int. Cl.
*A61B 5/04*  (2006.01)

(52) U.S. Cl.
USPC .......................................................... 600/513

(58) Field of Classification Search
USPC ............ 600/485, 486, 508, 509, 527; 607/2, 607/5, 9, 17–19
See application file for complete search history.

(56) References Cited

U.S. PATENT DOCUMENTS

| | | | |
|---|---|---|---|
| 5,643,327 | A | 7/1997 | Dawson et al. |
| 6,217,522 | B1 | 4/2001 | Shoshan |
| 7,286,875 | B1 | 10/2007 | Park et al. |
| 7,363,077 | B1 | 4/2008 | Min et al. |
| 2004/0030356 | A1 | 2/2004 | Osypka |
| 2005/0049646 | A1 | 3/2005 | Czygan et al. |
| 2007/0066898 | A1 | 3/2007 | Hendriks et al. |
| 2007/0129765 | A1 | 6/2007 | Gilkerson et al. |

FOREIGN PATENT DOCUMENTS

DE    103 61 143    12/2003

OTHER PUBLICATIONS

Espacenet Family list: DE10361143 (A1)—Mar. 24, 2005, 1 page.

*Primary Examiner* — Brian T Gedeon
(74) *Attorney, Agent, or Firm* — ARC IP Law, PC; Joseph J. Mayo (57) ABSTRACT

Embodiments relate to a heart monitor, which is connected to or can be connected to at least one sensor for pressure and volume data or equivalent substitute variables and which comprises an evaluation unit for processing at least one input signal reflecting the temporal course of pressure and volume data or equivalent substitute variables of the heart. The evaluation unit is configured such that it segments the input signal in accordance with individual completed cardiac cycles and examines segments of the input signal obtained in this way as to whether a particular segment of the input signal represents a PV diagram, which corresponds to specified quality conditions regarding the direction of circulation, morphology and distance between a starting and end values.

20 Claims, 3 Drawing Sheets

HEART MONITOR

This application takes priority from German Patent Application DE 10 2009 002 397.6, filed 15 Apr. 2009, the specification of which is hereby incorporated herein by reference.

BACKGROUND OF THE INVENTION

1. Field of the Invention

Embodiments of the invention relate to a heart monitor, which is connected, or can be connected to at least one sensor for pressure and volume data or equivalent substitute variables of a heart.

2. Description of the Related Art

A heart monitor is known, for example, from US 2004/0030356. The pressure and volume data obtained with such a heart monitor—similar to the way described in US 2004/0030356—is not currently, but could be used, for example, to optimize the stimulation parameters of an optionally implantable cardiac stimulator.

BRIEF SUMMARY OF THE INVENTION

The heart monitor described herein can be part of an implantable pulse generator, for example, such as a pacemaker or an implantable cardioverter/defibrillator (ICD).

It is a feature of one or more embodiments of the invention to create an improved heart monitor.

According to embodiments of the invention, this object is achieved by a heart monitor of the type mentioned above, which comprises an evaluation unit for processing at least one input signal reflecting the temporal course of pressure and volume data, or equivalent substitute variables of the heart, said evaluation unit being designed such that the evaluation unit segments the input signal in accordance with individual completed cardiac cycles and examines segments of the input signal obtained in this way as to whether a particular segment of the input signal represents a PV diagram, which corresponds to specified quality conditions regarding the direction of the loop, morphology and distance between a starting value and an ending value.

A PV diagram shall be understood as the two-dimensional representation of pressure and volume measurement data during a cardiac cycle, wherein the individual measurement points are connected according to the chronological order thereof.

PV diagrams are known in principle and can be used to determine clinically relevant parameters. For example, ventricular contractility, myocardial oxygen demand, an estimation of the cardiac efficiency, and the coordination of cardiac contractility and peripheral load can be determined. Previously, these parameters have only been available during a hospital stay. Continuous usage has therefore not been possible. The heart monitor according to embodiments of the invention has the advantage of enabling such continuous usage of the PV diagrams and, in this context, furthermore solves the problem of using, if possible, only those PV diagrams for further evaluation which can be attributed to plausible and stable measurement values. As a result, the heart monitor according to embodiments of the invention examines whether the PV diagram representing a particular cardiac cycle is stable and meets the specified quality conditions. Minor deviations are permitted, because they can, for example, be the result of fast autoregulation mechanisms and/or load changes.

The evaluation unit is preferably designed to evaluate consecutive signal value pairs of the input signal with respect to a direction of the loop of a PV diagram represented by the signal value pairs. For this purpose, the evaluation unit can be designed to determine the direction of the loop of a PV diagram represented by the signal value pairs by evaluating the rotation of two-dimensional vectors, in that it generates a two-dimensional coordinate system originating at the center of a particular PV diagram and determines, for each measurement point (signal value pair), a vector from the center of the coordinate system to a particular measurement point in order to determine the direction of the loop of consecutive measurement points. The direction of the loop of a PV diagram represented by the signal value pair is therefore a suitable criterion for examining the plausibility of the signal value pair, because a true PV diagram always has only one fixed direction of the loop. If the measurement values are supposed to represent a PV diagram having a reversal in the direction of the loop, this can only be attributed to a faulty signal value. Therefore, according to a preferred embodiment, the evaluation unit is designed to use the direction of the loop of a particular PV diagram represented by signal value pairs in order to detect and optionally correct invalid signal value pairs (these being signal value pairs which result in a direction of the loop counter to the general direction of the loop). This can be done, for example, in that the evaluation unit is designed to discard signal value pairs having a deviating direction of the loop.

Another preferred variant of a heart monitor relates to heart monitors having a marker signal input for marker signals which represent defined events within a particular cardiac cycle, including the time at which they occurred. The evaluation unit is preferably designed such that it segments the input signal on the basis of marker signals to be received via the marker signal input.

In addition, or as an alternative, the evaluation unit can also be designed to segment the input signal on the basis of morphological characteristics of the PV diagrams represented by the signal value pairs of the input signal.

A further alternative is to equip the heart monitor with an ECG signal input for an intracardiac ECG signal or surface ECG, wherein the evaluation unit is designed to segment the input signal on the basis of an intracardiac ECG signal to be received via the ECG signal input.

The evaluation unit can furthermore be designed to perform an approximation of the PV diagrams represented by the signal value pairs using substitute functions, such as ellipses, rectangles, trapezoids or the like. The selection of as favorable a geometry as possible can be done either manually and then be manually specified, or automatically by the evaluation unit.

With respect to a correction of potentially faulty signal value pairs, the evaluation unit is preferably designed to automatically detect and correct points of intersection of the PV diagrams represented by the signal value pairs which are the result of connecting consecutive signal value pairs. Such points of intersection are produced, for example, by measurement noise or measurement inaccuracies and do not occur in true PV diagrams.

With respect to the further evaluation, as described above, of corrected PV diagrams, the evaluation is designed to compare a particular corrected PV diagram to the respectively corresponding, original uncorrected PV diagram in order to derive quality characteristics. To this end, the evaluation unit is preferably designed to conduct the comparison on the basis of criteria, such as the number of corrected signal value pairs, the differences in the morphology of the represented PV diagrams, the area differences between the represented PV diagrams, focal point shifts between the PV diagrams, the distance between end and starting points of a particular PV diagram, or the like, and to compare and decide, as a function of the respective comparison result to specified quality criteria, as to whether or not a particular corrected PV diagram is suited for further evaluation.

In addition, the evaluation unit can be designed to enclose all signal value pairs representing a particular PV diagram with an envelope. To this end, the evaluation unit can be designed to determine the largest envelope possible, which encloses no, or the smallest envelope possible which encloses most or all signal value pairs of a signal segment representing a particular PV diagram.

As an alternative, the evaluation unit can also be designed to approximate a sequence of signal value pairs representing a particular PV diagram with one or more parameter-optimized functions.

The preliminarily evaluated signal value pairs described herein—or more specifically: sequences of signal value pairs of the input signal which represent a particular PV diagram—can subsequently be further evaluated. For this purpose, the evaluation unit is preferably designed to derive a value for one or more of the following parameters from a particular PV diagram (left or right ventricle) represented by signal value pairs:

Contractility index (Emax=ESP/(ESV−Vo)): Emax corresponds to the gradient of the line which, passing through Vo, just barely comes in contact with the PV curve at the left upper edge (see FIG. 3). The end-systolic pressure ESP is the pressure in the ventricle developing at the end of the ejection phase.

End-diastolic volume (EDV): The maximum amount of blood in the ventricle, measured at the end of the filling phase of each heart beat End-systolic volume (ESV): The minimum amount of blood in the ventricle, measured at the end of the cardiac ejection period Stroke volume (SV): The stroke volume of an individual heart beat (SV=EDV−ESV)

Ejection fraction (EF=SV/EDV)

Effective arterial elastance (Ea): The effective elastance of the arterial system coupled to the left ventricle (Ea=ESP/SV)

External work (EW): The fraction of the work performed by the heart that is directly converted into mechanical energy. This parameter is determined by calculating the area inside the PV curve.

Potential energy (PE): The fraction of the work performed by the heart that cannot be converted into mechanical energy. PE refers to an area connecting on the left to the PV curve. Starting from the residual volume (Vo), it runs over the line connecting Vo to the end-systolic pressure ESP, continues by following the isovolumetric relaxation, until the inflow valve opens and back to the Vo (see FIG. 3). Possibilities for directly determining Vo include the change in electrostimulation parameters such as AV and VV delay, heart rate, but also the artificial generation of extrasystoles, because the different end-systolic pressures are located on a line, the point of intersection of which corresponds to the volume axis, Vo. When substitute variables are used, these characteristics are transformed accordingly. Vo is estimated for this purpose, or determined from echocardiographic measurements.

Pressure-volume area (PVA): The entire energy demand of the heart during a beat (PVA=PE+EW). This variable can be used to determine the myocardial oxygen demand.

EW/PE: The efficiency of the heart can be determined from the ratio of EW to PE. The greater this ratio is, the higher is the portion of energy that the heart can convert into mechanical work. As an alternative, for the same purpose EW/PVA is used, which is to say the ratio of mechanical work performed to the entire energy demand of the heart.

Arterial-ventricular coupling (AVC): AVC=Ea/Emax=(ESV−Vo)/SV. This parameter can also be determined without measuring the left-ventricular pressure.

Preload recruitable stroke work (PRSW): Describes the ratio of EW to EDV and serves as a preload- and afterload-independent parameter for the myocardial contractility (alternative to Emax).

In order to calculate Emax, PE, PVA and AVC, the residual volume Vo must be determined. The residual volume is the amount of blood at which a contraction of the ventricle would result in an end-systolic pressure of 0 mmHg. This can be done using imaging methods, such as echocardiography, or it can be set to a sufficiently low fixed value if only changes are being analyzed. Vo is generally small compared to ESV.

According to preferred variants of the invention, the heart monitor can be connected to a cardiac stimulator and designed to influence the output of stimulation pulses by the cardiac stimulator. To this end, the evaluation, within the context of the further evaluation, is preferably designed to stimulate transient contractility changes (Emax), for example, by varying stimulation parameters, such as the atrioventricular delay (AVD), the interventricular delay (VVD), the stimulation rate or the like, in order to be able to determine a particular residual volume Vo.

As an alternative, the evaluation unit can also be designed to automatically determine the residual volume Vo, even without varying stimulation parameters, entirely without stimulating the heart in that the evaluation unit uses transient contractility changes to update the value of the residual volume Vo.

According to a likewise preferred variant, the heart monitor is connected to a cardiac stimulator and designed to influence the output of stimulation pulses by the cardiac stimulator, wherein the evaluation unit is further designed to use one of the above derived variables, such as Emax, EDV, ESV or the like, to simultaneously optimize an atrioventricular delay (AVD) and/or interventricular delay (VVD) and/or stimulation rate in that the atrioventricular delay (AVD) and/or interventricular delay (VDD) and/or stimulation rate are varied until a global optimum is obtained.

With respect to recording the measurement values, which ultimately—optionally after appropriate amplification or the like—produce the signal values of the input signal, the signal monitor is preferably connected to corresponding measurement sensors. These measurement sensors can be pressure sensors or force sensors, for example, or they can be distance sensors, as is explained below.

Pressure sensors used can be disposed, for example, in typical electrode leads of a cardiac stimulator, thereby enabling pressure measurement directly in a heart chamber. In order to determine the pressure in the left heart chamber, the pressure during the diastole can be determined by measuring the pressure in the left atrium and during the systole it can be determined by measuring the arterial pressure in the aorta.

A pressure sensor can also be integrated in a coronary sinus electrode lead. During a systole, the pressure in the coronary vessels rises as a result of the contraction of the myocardium. By measuring this pressure change, such as by way of a pressure sensor in a coronary sinus electrode lead, the ventricular pressure can be estimated.

Force sensors can be used, for example, to measure a force between two fixed points on the cardiac wall. This can be used for patients who have myocardial regions with non-contracting tissue.

In addition, or as an alternative, it is also possible to use a mechanical fixing device for positioning a coronary sinus electrode in order to capture the development of the force during the systole, and therefore indirectly the development of the pressure inside the heart chamber.

As a further alternative, local force or pressure sensors can be provided, which are introduced directly into the myocardium and can be used to determine the pressure development on the inside of the ventricle.

With respect to the use of distance sensors, it is conceivable to perform a distance measurement between two fixed points on the cardiac wall. This method can be used for patients who have myocardial regions with non-contracting tissue.

With respect to the use of pressure sensors that are connected to the heart monitor, it is also conceivable to dispose these in the septum between the heart chambers. These sensors can be designed such that they capture the pressure or a force development in the septum, or alternatively directly measure the ventricular pressure transseptally.

The heart monitor can also be connected to a pressure measurement catheter, by which long-term stable pressure measurements can be carried out in the ventricle or in the endocardium, in order to obtain measurement values which are transmitted to the heart monitor.

As an alternative, such pressure sensors can also be disposed on the inside of one or both ventricles, or in the endocardium, which contain a transmitter and transmit the measurement values thereof wirelessly to the heart monitor.

As an alternative, or in addition, the heart monitor can also be designed to determine ventricular pressures from substitute pressures, which are measured using pressure sensors attached to ventricular electrode leads, or pressure sensors attached to the inside or outside of the cardiac wall, or which were introduced into the pericardium in a minimally invasive manner.

As an alternative, or in addition, the heart monitor can also be designed to determine ventricular volumes from substitute variables (impedance measurement, ultrasonic propagation time measurement, damping of RF signals, damping of sound signals), which are measured using distance sensors attached to ventricular electrode leads or to the inside or outside of the cardiac wall, or which were introduced into the pericardium in a minimally invasive manner.

In an alternative, the heart monitor can also be designed to derive a ventricular pressure by evaluating an intracardiac impedance curve (such as by differentiation).

The determination of the intracardiac impedance curve required is known in principle and described in detail elsewhere.

The heart monitor can, in principle, be designed as an independent device, such as an independent implant. It can furthermore be part of an implantable medical device, such as a pacemaker or a cardioverter/defibrillator (ICD). The implantable medical device can also comprise an implant and an external device, which is connected telemetrically to the implant. The heart monitor of the type described here, and in particular the evaluation unit thereof, can be entirely or in parts thereof an integral part of the implant, or of the external device, or both, or other components of the medical device.

BRIEF DESCRIPTION OF THE DRAWINGS

Embodiments of the invention will now be described in more detail with reference to an exemplary embodiment illustrated the figures. Shown are.

DETAILED DESCRIPTION OF THE INVENTION

Figure 1:
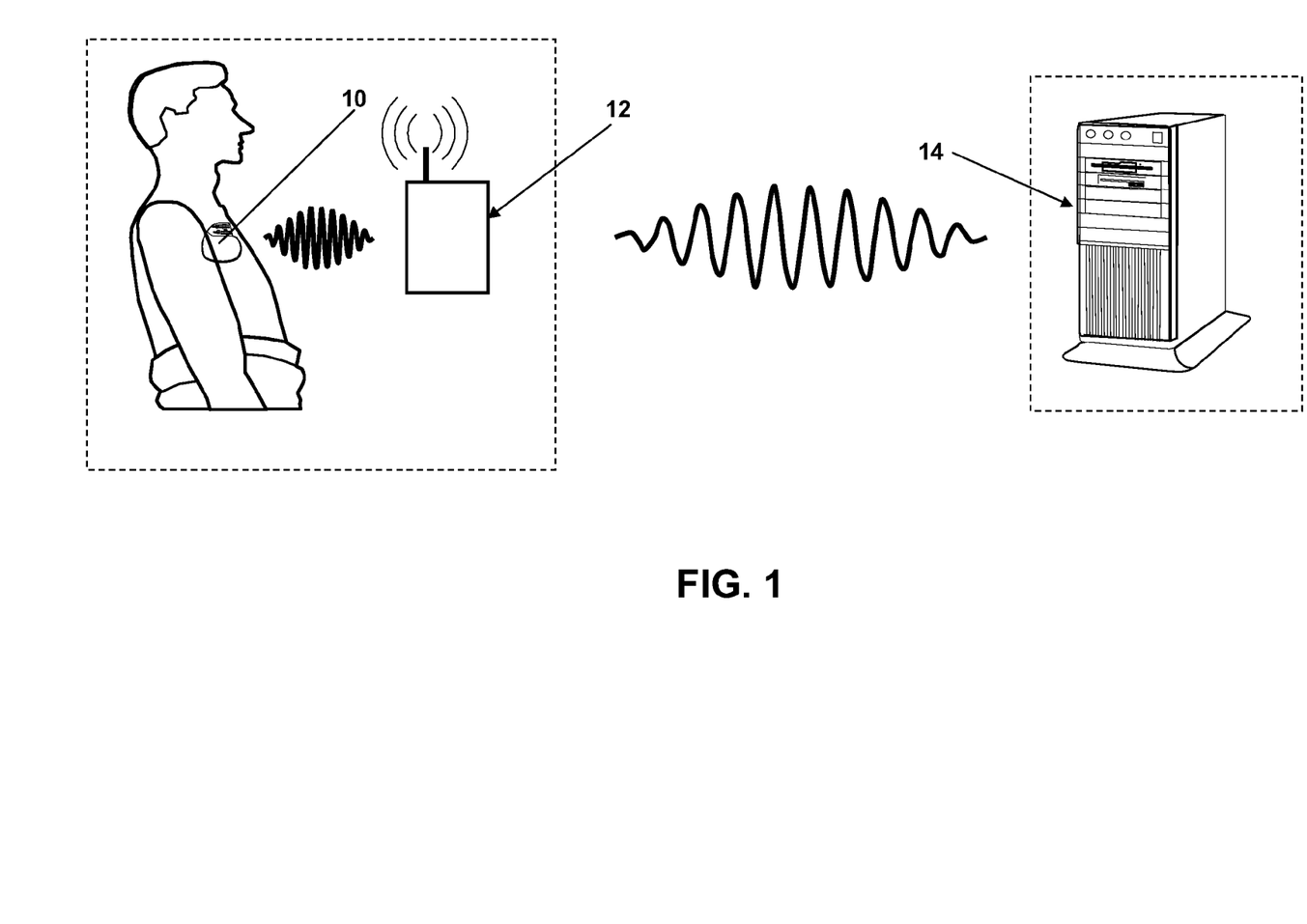
FIG. 1: A medical device, comprising an implant and an external device and a central service center.

FIG. 1 shows an implantable medical device in the form of a pacemaker (10) and an external device (12), also referred to as patient device, which is connected in a manner which is known per se at least part of the time to the pacemaker (10) by way of appropriate wireless data communication interfaces. The external device (12) is furthermore connected at least part of the time to a central service center (14). The configuration illustrated in FIG. 1 allows data recorded by the pacemaker (10) to be processed, both directly in the pacemaker (10) and, for example, also in the external device (12) or in the central service center (14).

Figure 2:
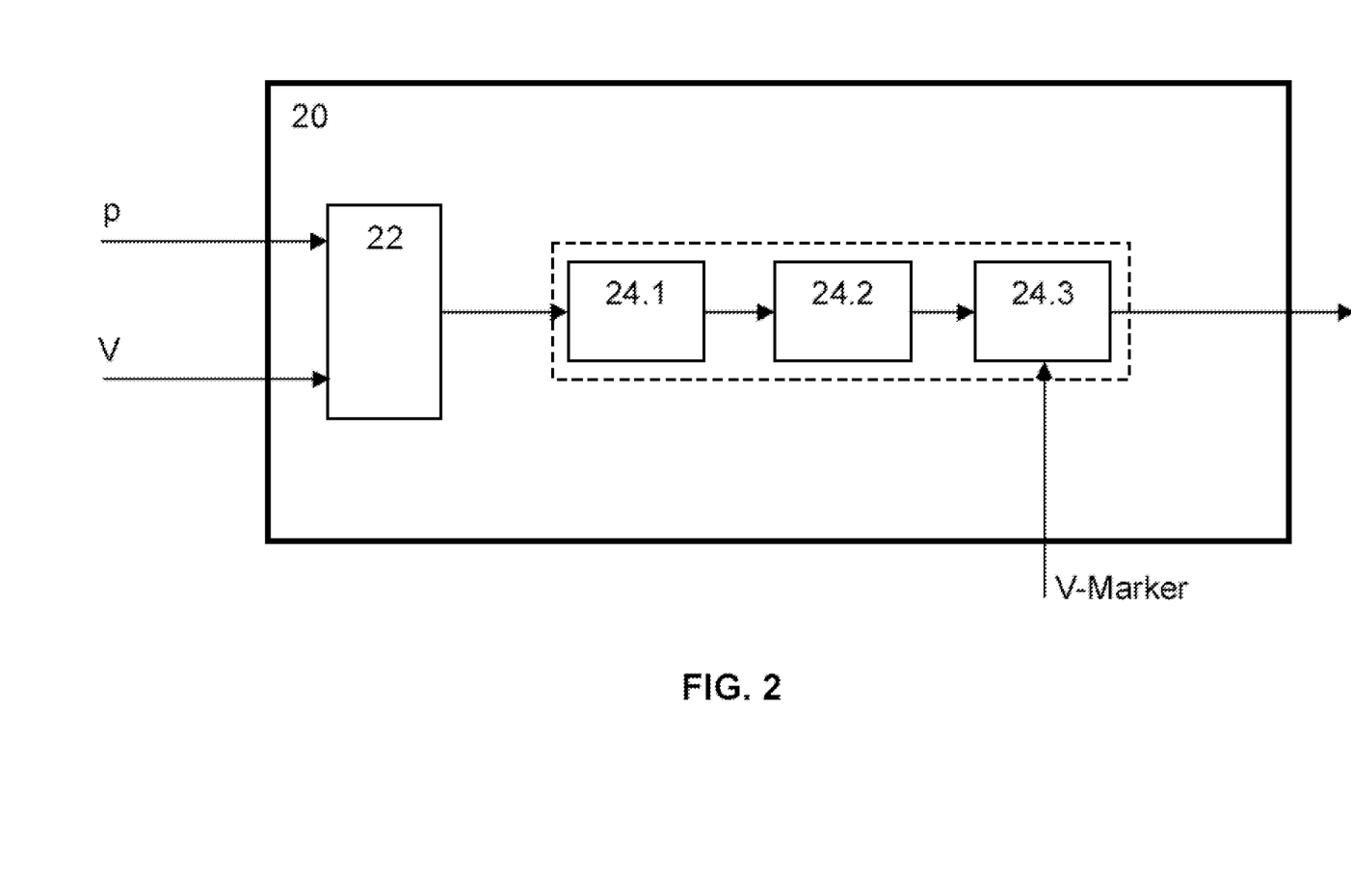
FIG. 2: a heart monitor as a medical device or part of a medical device.

FIG. 2 shows a heart monitor (20) according one or more embodiments of the invention, which can be part of the pacemaker (10) of FIG. 1. The heart monitor (20) comprises a signal input for receiving pressure or volume data or equivalent substitute variables of heart. These form an input signal of the heart monitor (20). The signal input can be connected to further components of the pacemaker (10), or it can also be directly connected to suitable measurement sensors, such as pressure or force sensors. The pacemaker is preferably designed in a manner which is known per se to determine a ventricular volume by way of intraventricular impedance measurement. The impedance to be measured inside a ventricle of a heart is decisively determined by the amount of blood enclosed by the ventricle, because the blood has higher conductivity that the surrounding heart tissue (myocardium). The measurements of the intracardiac impedance, and in particular of the intraventricular impedance, and the evaluation of the impedance curve for determining a ventricular volume are known in principle and therefore need not be described in detail here.

Measured variables which represent a pressure present in the ventricle can be recorded, for example, by way of a pressure measurement sensor disposed in the ventricle. This sensor, as indicated above, can be part of a ventricular electrode lead of the pacemaker (10). The pressure sensor can also be an independent sensor, which is designed to transmit pressure measurement values wirelessly to the signal input of the heart monitor (20). The pressure measurement sensor can act, for example, passively in the manner of a transponder. Further methods and sensors for determining the pressure present in the ventricle have been indicated at the beginning.

In the embodiment illustrated here, the signal input (22) of the heart monitor (20) has two inputs, which is to say an input for pressure measurement values or equivalent variables, and a second input for volume measurement values or equivalent variables. This produces a two-channel input signal, the signal values of which are formed by a pair of values, of which one value represents a pressure measurement value and the other value represents a volume measurement value. The value pairs are numbered in the chronological order thereof.

Figure 3:
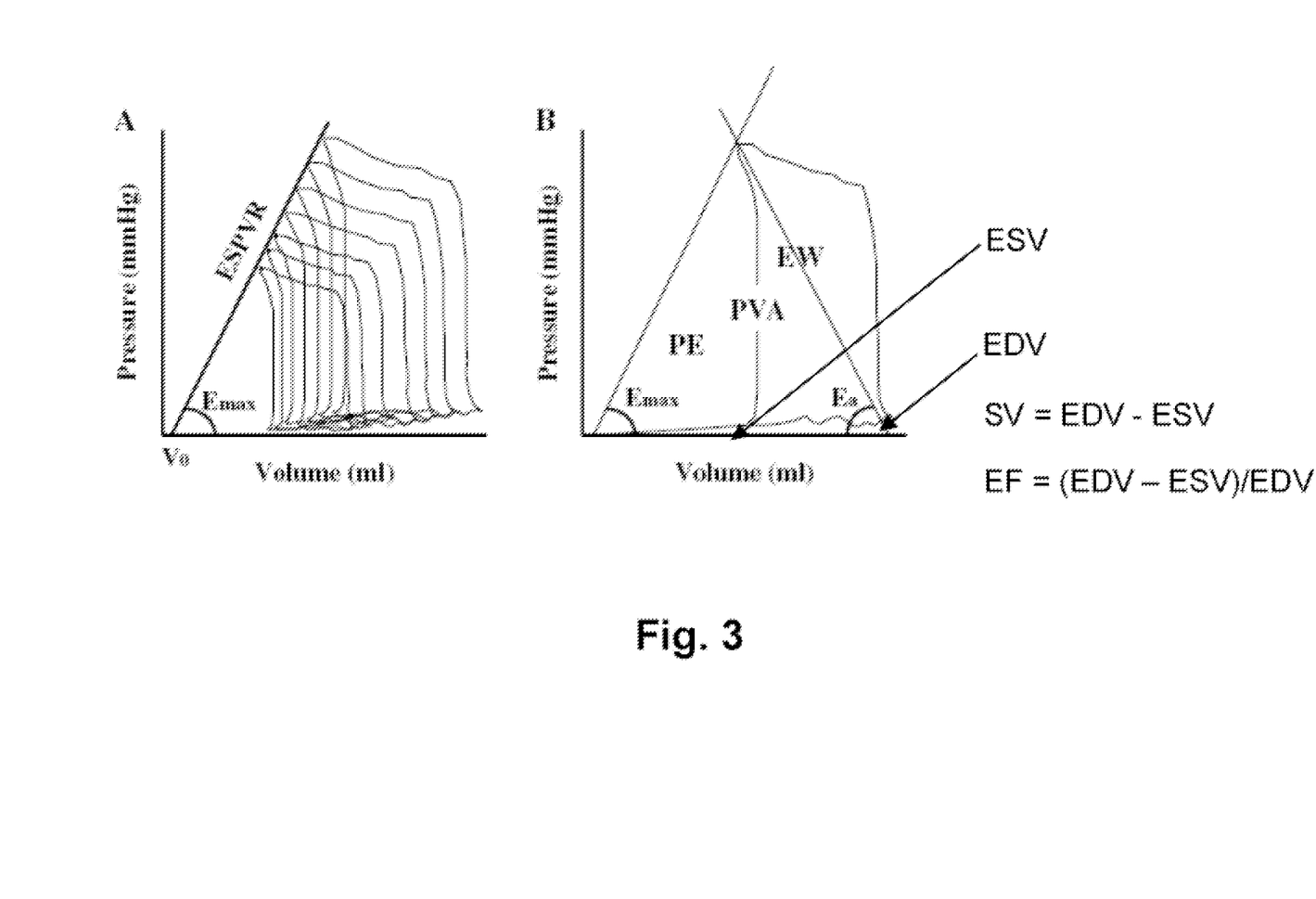
FIG. 3: diagrams for illustrating a pressure-volume curve inside a ventricle and variables that can be derived therefrom.

This signal input (22) of the heart monitor (20) is connected to an evaluation unit (24), which has a three-stage design, as is indicated in FIG. 2. A first stage of the evaluation unit (24) is designed to segment the input signal, comprising the signal value pairs, such that each segment of the input signal reflects a cardiac cycle. In the embodiment shown, this is done in that the first stage (24.1) of the evaluation unit (24) is connected to a marker signal input, which is connected to the marker channel, which is known per se, of the pacemaker (10). By way of the marker signal input (26), the first stage (24.1) of the evaluation unit (24) can receive marker signals, which represent the occurrence and the respective time of a cardiac event, such as an R-wave. Such marker signals are known in principle and need not be explained in detail here. The first stage (24.1) of the evaluation unit (24) segments the input signal on the basis of the one-time event per cardiac cycle represented by the marker signal. Each segment of the input signal obtained in this way represents a cardiac cycle and additionally represents a PV diagram, which represents the course of the pressure in the ventricle against the course of the volume in the ventricle. Diagrams are shown in FIG. 3 by way of example.

The evaluation unit (24) conducts the above-described analysis of the direction of the loop of the PV diagram represented by the signal value pairs in that it generates a two-dimensional coordinate system originating at the center of a particular PV diagram and determines, for each measurement point (signal value pair), a vector from the center of the coordinate system to the respective measurement point in order to determine the direction of the loop of consecutive measurement points. This direction should be monotonic in one direction. If isolated signal value pairs bring about a reversal of the direction of the loop, these signal value pairs are eliminated or corrected. In line with these evaluations of the input signal by the second evaluation stage (24.2) of the evaluation unit (24), the second evaluation stage (24.2) of the evaluation unit (24) can also have the above-described properties, which result in a preliminary evaluation of a particular sequence of the input signal, which is to say, for example, it can be designed to detect and eliminate points of intersection of the PV diagrams represented by the signal value pairs.

The evaluation unit (24) furthermore comprises a second evaluation stage (24.2), which preliminarily evaluates every segment of the input signal as described above in that the second evaluation stage (24.2) of the evaluation unit (24) analyzes every segment of the input signal as to whether the respective segment of the input signal represents a PV diagram for which the quality characteristics derived correspond to the quality criteria. For this purpose, the second evaluation stage (24.2) of the evaluation unit (24) is designed to compare a corrected input signal segment it generated to the respectively original segment of the input signal (morphology, area, ratio of circumference to area, distance between starting and end points, or number of the measurement values) and to decide as a function of a comparison result whether or not the correct PV diagram is suited for further evaluation.

A third evaluation stage (24.3) of the evaluation unit (24) finally is designed to process the corrected input signal segments generated by the second evaluation stage (24.2) such that the third evaluation stage (24.3) derives a value (28) for one or more of the following parameters from these input signal segments:

contractility index (Emax=ESP/(ESV−Vo)): Emax corresponds to the gradient of the line which, passing through Vo, just barely comes in contact with the PV curve at the left upper edge (see FIG. 3).

End-diastolic volume (EDV): The maximum amount of blood in the ventricle, measured at the end of the filling phase of each heart beat End-systolic volume (ESV): The minimum amount of blood in the ventricle, measured at the end of the cardiac ejection period Stroke volume (SV): The stroke volume of an individual heart beat (SV=EDV−ESV)

Ejection fraction (EF=SV/EDV)

Effective arterial elastance (Ea): The effective elastance of the arterial system coupled to the left ventricle (Ea=ESP/SV)

External work (EW): The fraction of the work performed by the heart that is directly converted into mechanical energy. This parameter is determined by calculating the area inside the PV curve.

Potential energy (PE): The fraction of the work performed by the heart that cannot be converted into mechanical energy. PE refers to an area connecting on the left to the PV curve. Starting from the residual volume (Vo), it runs over the line connecting Vo to the end-systolic pressure, continues by following the isovolumetric relaxation, until the inflow valve opens and back to the Vo (see FIG. 3). Possibilities for directly determining Vo include the change in electrostimulation parameters such as AV and VV delay, heart rate, but also the artificial generation of extrasystoles, because the different end-systolic pressures are located on a line, the point of intersection of which corresponds to the volume axis, Vo. When substitute variables are used, these characteristics are transformed accordingly. Vo is estimated for this purpose, or determined from echocardiographic measurements.

Pressure-volume area (PVA): The entire energy demand of the heart during a beat (PVA=PE+EW). This variable can be used to determine the myocardial oxygen demand.

EW/PE: The efficiency of the heart can be determined from the ratio of EW to PE. The greater this ratio is, the higher is the portion of energy that the heart can convert into mechanical work. As an alternative, for the same purpose EW/PVA is used, which is to say the ratio of mechanical work performed to the entire energy demand of the heart.

Arterial-ventricular coupling (AVC): AVC=Ea/Emax=(ESV−Vo)/SV. This parameter can also be determined without measuring the left-ventricular pressure.

Preload recruitable stroke work (PRSW): Describes the ratio of EW to EDV and serves as a preload- and afterload-independent parameter for the myocardial contractility (alternative to Emax).

Several of these parameters are illustrated again in the PV diagrams shown by way of example in FIG. 3.

The evaluation unit (24), and in particular the third evaluation stag (24.3) thereof, is connected to a control unit and/or at least one stimulation unit of the pacemaker (10) such that the evaluation unit (24) can influence the output of stimulation pulses by the pacemaker (10) by way of the electrode leads thereof.

As is known in principle, the pacemaker (10) acts as a cardiac stimulator and as such is designed to output electric stimulation pulses in the manner known per se to the myocardium of a particular chamber (ventricle or atrium) of a heart by way of electrode leads connected via a cardiac stimulator, in order to trigger a stimulated contraction of the respective cardiac chamber in this way.

The behavior of a stimulated heart decisively depends on the time at which stimulation pulses are output to the different chambers of a heart. The decisive time intervals in the control of a cardiac stimulator are an atrioventricular delay (AVD) and interventricular delay (VDD), which in the case of the pacemaker (10) shown in FIG. 1 can be influenced by the evaluation unit (24) of the heart monitor (20).

Specifically, the evaluation unit (24) is designed to vary the duration of a particular atrioventricular delay and a particular interventricular delay in order to determine the residual volume Vo in this way, which is required for determining the contractility index (Emax). As an alternative, the heart rate can be specifically modulated for the determination of the residual volume in order to implement a change in the filling level at the start of the systole and therefore a preload variation.

In addition, the evaluation unit (24) is designed to vary the atrioventricular delay and/or the interventricular delay and/or the stimulation rate, in order to determine in this way optimized variables which are matched to each other for the atrioventricular delay and/or the interventricular delay and/or the stimulation rate, for which a global optimum is obtained for the variables derived from the pressure-volume diagram by the third evaluation stage (24.3).

As indicated before, the different components of the heart monitor (20) can be distributed among different physical entities, such as the pacemaker (10) and the external or patient device (12) or also the central service center (14).

However, it is preferred that the heart monitor (20) as a whole is part of the implantable pacemaker (10). The parameter values generated by the third evaluation stage (24.3) of the heart monitor (20) and derived from the input signal are additionally present at an output (28) of the third evaluation stage (24.3) of the evaluation unit (24). This output (28) is preferably connected to a memory and/or a telemetry unit of the pacemaker (10) in order to be able to transmit in this way the derived parameter values telemetrically to the patient device (12) and from there to the central service center (14). The central service center (14) can be designed to derive further values, such as trends reflecting the development of the parameter values, from the derived parameter values it receives and forward them or make them available to a treating physician.

In this way, the heart monitor (20) can be used, for example, to monitor the efficacy of a cardiac resynchronization therapy (CRT) or to conduct better long-term monitoring using clinically recognized parameters.

As a result, expanded optimization possibilities of the implant parameters are attained (which is to say the setting variables of the pacemaker) due to a more precise determination of a present state of the heart. In addition, it is also possible to draw conclusions of the peripheral system using the PV diagrams obtained according to one or more embodiments of the invention.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A heart monitor, which is connected to or can be connected to at least one sensor associated with pressure and volume data or equivalent substitute variables and which comprises:
    an evaluation unit configured to process input signals that reflect a temporal course of pressure and volume data or equivalent substitute variables of a heart;
    said evaluation unit further configured to
        segment the input signals into segments in accordance with individual completed cardiac cycles,
        examine said segments of the input signals and determine whether a particular segment of the input signals represents a PV diagram, which corresponds to specified quality conditions, and
        evaluate consecutive signal value pairs of the input signals with respect to a direction of a loop of the PV diagram represented by the consecutive signal value pairs.

2. The heart monitor according to claim 1, wherein the evaluation unit is further configured to
    determine the direction of the loop of the PV diagram represented by the consecutive signal value pairs through evaluation of a direction of two-dimensional vectors, through generation of a center of a two-dimensional coordinate system that originates at a center of a particular PV diagram, and
    determine for each measurement point or signal value pair, a vector from the center of the two-dimensional coordinate system to a particular measurement point in order to determine the direction of the loop of consecutive measurement points.

3. The heart monitor according to claim 1, wherein the evaluation unit is further configured to detect and optionally correct the direction of the loop of the particular PV diagram represented by the consecutive signal value pairs in order to produce a corrected PV diagram.

4. The heart monitor according to claim 3, wherein the evaluation unit is further configured to discard signal value pairs which have a deviating direction of the loop in order to produce the corrected PV diagram.

5. The heart monitor according to claim 3, wherein the evaluation unit is further configured to compare corrected PV diagrams to a respective original, uncorrected PV diagram prior to further evaluation.

6. The heart monitor according to claim 5, wherein the evaluation unit is further configured to compare based on quality criteria, such as a number of corrected or discarded signal value pairs, differences in morphology, area differences, ratio of a circumference to area, focal point shifts, a distance between end and starting points, and, as a function of a respective comparison result, determine whether or not a particular corrected PV diagram is suited for further evaluation.

7. The heart monitor according to claim 1, further comprising:
    a marker signal input configured to receive marker signals; and,
    wherein said marker signals represent defined events within a particular cardiac cycle, including a time at which said defined events have occurred, wherein the evaluation unit is further configured to segment the input signals based on the marker signals as received via the marker signal input.

8. The heart monitor according to claim 1, wherein the evaluation unit is further configured to segment the input signals based on morphological characteristics of PV diagrams represented by signal value pairs of the input signals, and/or to perform an approximation of the PV diagrams represented by the signal value pairs using substitute functions, or ellipses, rectangles, or trapezoids, in order to obtain a corrected PV diagram and/or to automatically detect and correct points of intersection of the PV diagrams which are represented by the signal value pairs and obtained by connecting consecutive signal value pairs, in order to produce the corrected PV diagram and/or in order to obtain the corrected PV diagram through calculation of an envelope that encloses all measurement points and/or to approximate a sequence of signal value pairs, each representing the PV diagram, by way of one or more parameter-optimized functions in order to obtain the corrected PV diagram.

9. The heart monitor according claim 1, comprising an ECG signal input associated with an intracardiac ECG signal or surface ECG, wherein the evaluation unit is further configured to segment the input signals based on the intracardiac ECG signal received via the ECG signal input.

10. The heart monitor according to claim 8, wherein the evaluation unit is further configured to determine a largest envelope possible, which encloses no signal segment that represents a particular PV diagram, or a smallest possible envelope, which encloses a highest number of measurement points of a signal segment that represents a particular PV diagram.

11. The heart monitor according to claim 1, wherein the evaluation unit is further configured to derive a value for one or more parameter from a particular PV diagram represented by signal value pairs within the context of a further evaluation wherein said one or more parameter comprises:
Contractility index or Emax,
End-diastolic volume or EDV,
End-systolic volume or ESV,
Stroke volume SV,
Ejection fraction or EF or SV/EDV,
Effective arterial elastance or Ea,
External work or EW,
Potential energy or PE,
Pressure volume area or PVA,
Quotient from external work and potential energy or EW/PE,
Arterial-ventricular coupling or AVC or Ea/Emax,
End-systolic pressure or ESP,
Preload recruitable stroke work or PRSW.

12. The heart monitor according to claim 11, wherein the heart monitor is connected to a cardiac stimulator and configured to influence the output of stimulation pulses by the cardiac stimulator:
wherein the evaluation unit is further configured to stimulate local changes in a filling level or the contractility index or Emax, within a context of the further evaluation, through variation of stimulation parameters that comprise one or more of atrioventricular delay or AVD, interventricular delay or VVD and/or cardiac cycle duration, in order to determine a particular residual volume Vo, or
wherein the evaluation unit is further configured to use one of said parameters to simultaneously optimize the atrioventricular delay or AVD and/or the interventricular delay or VVD and/or a stimulation rate, in that the atrioventricular delay or AVD and/or the interventricular delay or VVD and/or the stimulation rate are varied until a global optimum of one or more of said parameters has been achieved.

13. The heart monitor according to claim 11, wherein, within the context of the further evaluation, the evaluation unit is further configured to employ automatic detection of transient changes of the contractility index or Emax, of preload, or afterload, and to update a particular value of residual volume Vo.

14. The heart monitor according to claim 11, wherein the values of said parameters are determined over time and stored and wherein curves of said parameters with respect to said time are used to observe a patient or used as input variables for prediction algorithms.

15. A heart monitor, which is connected to or can be connected to at least one sensor associated with pressure and volume data or equivalent substitute variables and which comprises:
an evaluation unit configured to process input signals that reflect a temporal course of pressure and volume data or equivalent substitute variables of a heart;
said evaluation unit further configured to
segment the input signals into segments in accordance with individual completed cardiac cycles,
examine said segments of the input signals and determine whether a particular segment of the input signals represents a PV diagram, which corresponds to specified quality conditions, and
segment the input signals based on morphological characteristics of PV diagrams represented by signal value pairs of the input signals, and/or to perform an approximation of the PV diagrams represented by the signal value pairs using substitute functions, or ellipses, rectangles, or trapezoids, in order to obtain a corrected PV diagram and/or to automatically detect and correct points of intersection of the PV diagrams which are represented by the signal value pairs and obtained by connecting consecutive signal value pairs, in order to produce the corrected PV diagram and/or in order to obtain the corrected PV diagram through calculation of an envelope that encloses all measurement points and/or to approximate a sequence of signal value pairs, each representing the PV diagram, by way of one or more parameter-optimized functions in order to obtain the corrected PV diagram.

16. The heart monitor according to any one of claim 15, wherein the evaluation unit is further configured to
evaluate consecutive signal value pairs of the input signals with respect to a direction of a loop of the PV diagram represented by the consecutive signal value pairs,
detect and optionally correct the direction of the loop of the particular PV diagram represented by the consecutive signal value pairs in order to produce a corrected PV diagram, and
discard signal value pairs which have a deviating direction of the loop in order to produce the corrected PV diagram.

17. The heart monitor according to claim 16, wherein the evaluation unit is further configured to
determine the direction of the loop of the PV diagram represented by the consecutive signal value pairs through evaluation of a direction of two-dimensional vectors, through generation of a center of a two-dimensional coordinate system that originates at a center of a particular PV diagram, and
determine for each measurement point or signal value pair, a vector from the center of the two-dimensional coordinate system to a particular measurement point in order to determine the direction of the loop of consecutive measurement points.

18. The heart monitor according to claim 15, wherein the evaluation unit is further configured to determine a largest envelope possible, which encloses no signal segment that represents a particular PV diagram, or a smallest possible envelope, which encloses a highest number of measurement points of a signal segment that represents a particular PV diagram.

19. The heart monitor according to claim 15, wherein the evaluation unit is further configured to detect and optionally correct the direction of the loop of the particular PV diagram represented by the consecutive signal value pairs in order to produce a corrected PV diagram.

20. A heart monitor, which is connected to or can be connected to at least one sensor associated with pressure and volume data or equivalent substitute variables and which comprises:
an evaluation unit configured to process input signals that reflect a temporal course of pressure and volume data or equivalent substitute variables of a heart;
said evaluation unit further configured to
segment the input signals into segments in accordance with individual completed cardiac cycles,
examine said segments of the input signals and determine whether a particular segment of the input signals represents a PV diagram, which corresponds to specified quality conditions,
evaluate consecutive signal value pairs of the input signals with respect to a direction of a loop of the PV diagram represented by the consecutive signal value pairs, and
segment the input signals based on morphological characteristics of PV diagrams represented by signal value pairs of the input signals, and/or to perform an approximation of the PV diagrams represented by the signal value pairs using substitute functions, or ellipses, rectangles, or trapezoids, in order to obtain a corrected PV diagram and/or to automatically detect and correct points of intersection of the PV diagrams which are represented by the signal value pairs and obtained by connecting consecutive signal value pairs, in order to produce the corrected PV diagram and/or in order to obtain the corrected PV diagram through calculation of an envelope that encloses all measurement points and/or to approximate a sequence of signal value pairs, each representing the PV diagram, by way of one or more parameter-optimized functions in order to obtain the corrected PV diagram;
wherein the evaluation unit is further configured to determine a largest envelope possible, which encloses no signal segment that represents a particular PV diagram, or a smallest possible envelope, which encloses a highest number of measurement points of a signal segment that represents a particular PV diagram.

* * * * *